(12) United States Patent
Mak et al.

(10) Patent No.: US 6,319,913 B1
(45) Date of Patent: *Nov. 20, 2001

(54) PENETRATION ENHANCING AND IRRITATION REDUCING SYSTEMS

(75) Inventors: Vivien H. W. Mak, Menlo Park; Stephen Grayson, San Rafael, both of CA (US)

(73) Assignee: Cellegy Pharmaceuticals, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/189,090

(22) Filed: Nov. 9, 1998

Related U.S. Application Data

(60) Provisional application No. 60/064,980, filed on Nov. 10, 1997.

(51) Int. Cl.[7] ..................................................... A61K 31/56
(52) U.S. Cl. ............................................. 514/179; 514/182
(58) Field of Search ..................................... 514/784, 947, 514/946; 424/448, 449

(56) References Cited

U.S. PATENT DOCUMENTS

| | | | |
|---|---|---|---|
| 4,537,776 | 8/1985 | Cooper | 514/424 |
| 4,552,872 | 11/1985 | Cooper et al. | 514/175 |
| 4,863,970 | 9/1989 | Patel et al. | 514/784 |
| 5,391,548 * | 2/1995 | Francoeur et al. | 514/213 |
| 5,601,839 * | 2/1997 | Quan et al. | 514/784 |
| 5,607,691 * | 3/1997 | Hale et al. | 424/449 |
| 5,760,096 | 6/1998 | Thornfeldt et al. | 514/946 |
| 5,952,000 * | 9/1999 | Venkateshwa | 424/448 |

FOREIGN PATENT DOCUMENTS

| | | | |
|---|---|---|---|
| 0 043 738 A2 | 1/1982 | (EP) | A61K/9/06 |
| 0 043 738 B1 | 1/1982 | (EP) . | |

OTHER PUBLICATIONS

Bronaugh, R.L., et al., "Methods for In Vitro Percutaneous Absorption Studies VII: Use of Excised Human Skin" *J. Pharm. Sci.* 75(11):1094–1097.

* cited by examiner

Primary Examiner—William R. A. Jarvis
Assistant Examiner—Vickie Kim
(74) *Attorney, Agent, or Firm*—Townsend and Townsend and Crew, LLP

(57) ABSTRACT

This invention lies in the technology of transdermal and topical drug delivery. In particular, the present invention relates to enhancement of the penetration of transdermally or topically applied drugs and with the reduction of skin irritation that often accompanies transdermal and topical drug delivery.

26 Claims, 2 Drawing Sheets

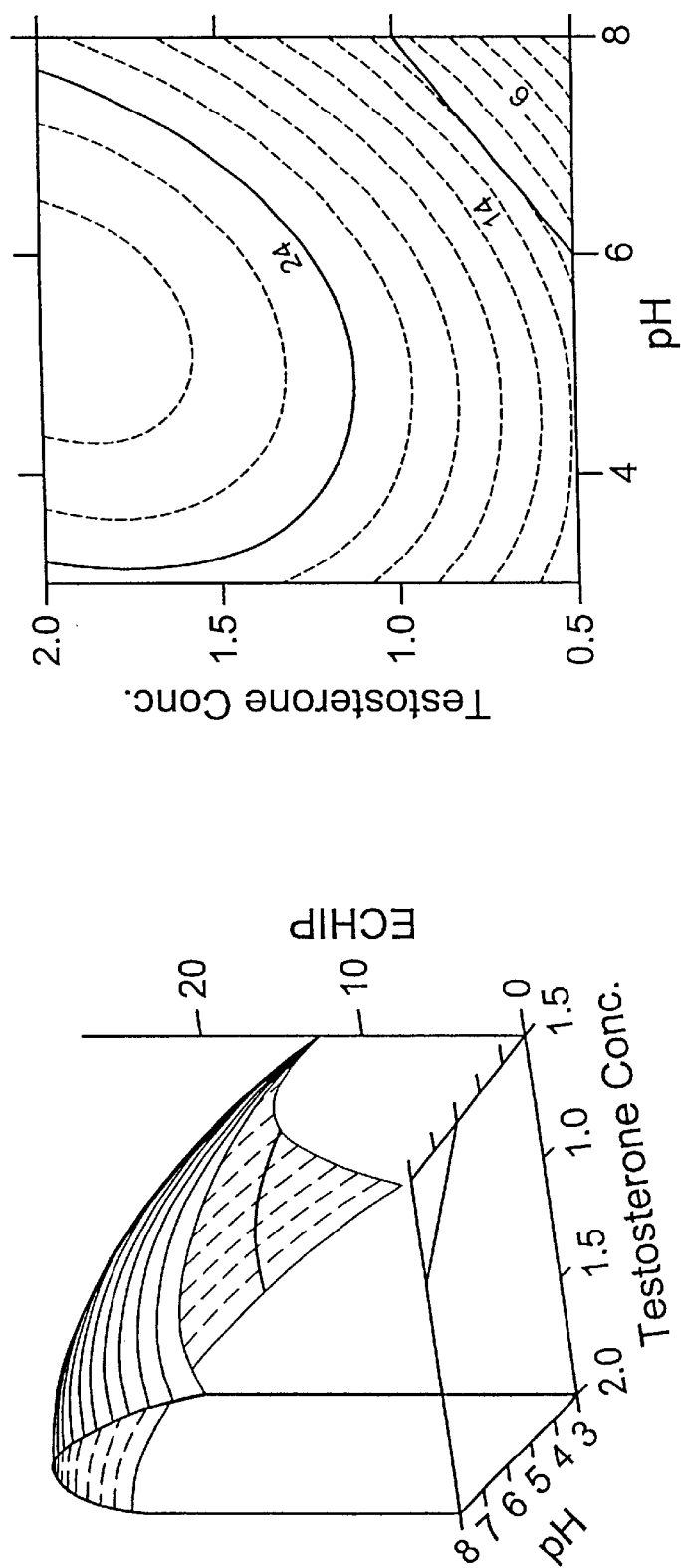

PENETRATION ENHANCING AND IRRITATION REDUCING SYSTEMS

This application claims benefit of Provisional No. 60/064,980 filed Nov. 10, 1997.

FIELD OF INVENTION

This invention lies in the technology of transdermal and topical drug delivery. In particular, the present invention relates to enhancement of the penetration of transdermally or topically applied drugs and to reduction of the skin irritation that often accompanies transdermally and topically applied drug delivery.

BACKGROUND OF THE INVENTION

During the past decade, the feasibility of the dermal route for systemic drug delivery has been established. Transdermal therapeutic systems include those containing scopolamine, glyceryl trinitrate, clonidine, fentanyl, nicotine and estradiol. However, one drawback with drugs applied to the skin or mucous membrane is that they frequently cause irritation. Additionally, many of the necessary components of topical, transdermal, and transmucosal formulations and delivery devices, such as solubilizing agents, suspending agents, dispersing agents, preservatives, animal and vegetable fats, oils, or waxes, stabilizing agents, thickening or gelling agents, buffering agents, adhesive agents, and, particularly, penetration enhancing agents, are irritating alone or in combination. However, in the absence of penetration enhancing agents, few drugs are capable of penetrating the skin or mucous membranes in therapeutically effective concentrations. Typically, using penetration enhancing compounds, processes or devices to increase drug penetration solves this problem. Included among these are chemical enhancers, iontophoresis, sonophoresis, and various delivery devices.

In most instances, penetration enhancement usually results in unwanted irritation. Many transdermal and topical products show high incidences of adverse skin reactions such as scaling, pruritic erythema, and vesicobollous irritant and allergic contact dermatitis. This is particularly true for topical and transdermal testosterone products currently on the market. Formulations comprised of combinations of ingredients of the same type instead of only one ingredient of that type, such as using a combination of two solvents instead of just one solvent, have been reported to lessen irritation without lowering drug permeation. This approach has also been applied to penetration enhancing agents. In particular, the use of glycerol, polyglycerol ethers, or dexpanthenol in combination with other penetration enhancing agents has been reported to lessen irritation. Using mixtures of penetration enhancers of different polarities and modes of action has also been reported to increase drug permeability without necessitating the use of higher concentrations of irritating penetration enhancers. The problem has also been approached by the additional inclusion of non-irritating ingredients such as glycerin.

U.S. Pat. No. 5,760,096, which issued to Thornfeldt et al. on Jun. 2, 1998, discloses a penetration enhancing system based on the use of various combinations of known penetration enhancing excipients. One type of penetration system disclosed combines an alcohol and a glycol, at glycol:alcohol weight ratios of about 1:0.1 to about 1:10, with one or more excipients categorized as surfactants, branched chain fatty acid esters, or membrane fluidizers.

In addition, U.S. Pat. No. 4,863,970, which issued to Patel et al. on Sep. 5, 1989, discloses a penetration-enhancing binary mixture of a cell-envelope-disordering compound and a lower alcohol. The binary mixtures can optionally contain inert ingredients that are soluble within the enhancer compositions. Neither Thornfeldt et al. nor Patel et al t. teach or disclose the beneficial use of oleic acid in favor of oleyl alcohol. In addition, the use of a gelling agent in combination with oleic acid is not disclosed.

Ultimately, the success of transdermal systems depends on the ability of the drug to permeate the skin in sufficient quantities to achieve the desired therapeutic effect. However, the transdermal system's ability for skin permeation is tempered by the irritation side effect that it can cause. There is a need in the art for a transdermal therapeutic system that has good penetration, but that has little unwanted skin and mucous membrane irritation. The present invention fulfills this and other needs.

SUMMARY OF THE INVENTION

The compositions of the present invention relate to a penetration enhancing system (PES) that can be utilized in many types of products for topical or transdermal application, that include, but are not limited to, solutions, creams, lotions, ointments, gels, aerosols and patch devices. In certain aspects, the present invention relates to a composition for topical application having penetration-enhancing properties, the composition comprising an active agent; and a penetration-enhancing system that comprises oleic acid; a $C_1$–$C_4$ alcohol; and a glycol. Optionally, the composition further comprises a gelling agent. In preferred embodiments, the gelling agent is CARBOPOL® which is a polyacrylic acid. In certain embodiments, the preferred active ingredient is testosterone or a testosterone derivative.

The penetration enhancing system of the present invention effectively enhances delivery of transdermally and/or topically active substances, while surprisingly reducing skin irritation caused by the application of irritating substances to the skin. The penetration enhancing system of the present invention can also be used for mucosal delivery.

In another aspect, the present invention relates to a method for administering a topically or systemically active agent, the method comprising: topically administering to a mammal a composition comprising: a) an active agent; and b) a penetration-enhancing system comprising: (i) oleic acid; (ii) a $C_1$–$C_4$ alcohol; and (iii) a glycol. Optionally, the penetration-enhancing system further comprises (iv) a gelling agent. In certain preferred embodiments, the method relates to treatment of conditions related to testosterone deficiency.

In yet another aspect, the present invention relates to a method of reducing inflammation associated with topical application of an active agent, the method comprising: topically administering to a terrestrial mammal a composition comprising: a) an active agent; and b) a penetration-enhancing system comprising: (i) oleic acid; (ii) a $C_1$–$C_4$ alcohol; and (iii) a glycol. In certain embodiments, the penetration-enhancing system further comprises (iv) a gelling agent. Typically, the inflammation is associated with the skin.

Further combinations, compositions and aspects of the present invention will be apparent with the following detailed description.

BRIEF DESCRIPTION OF THE DRAWINGS

FIG. 2 illustrates the influence of solution pH and concentration of testosterone of the formulations of the present invention.

DETAILED DESCRIPTION AND PREFERRED EMBODIMENTS

Figure 1:
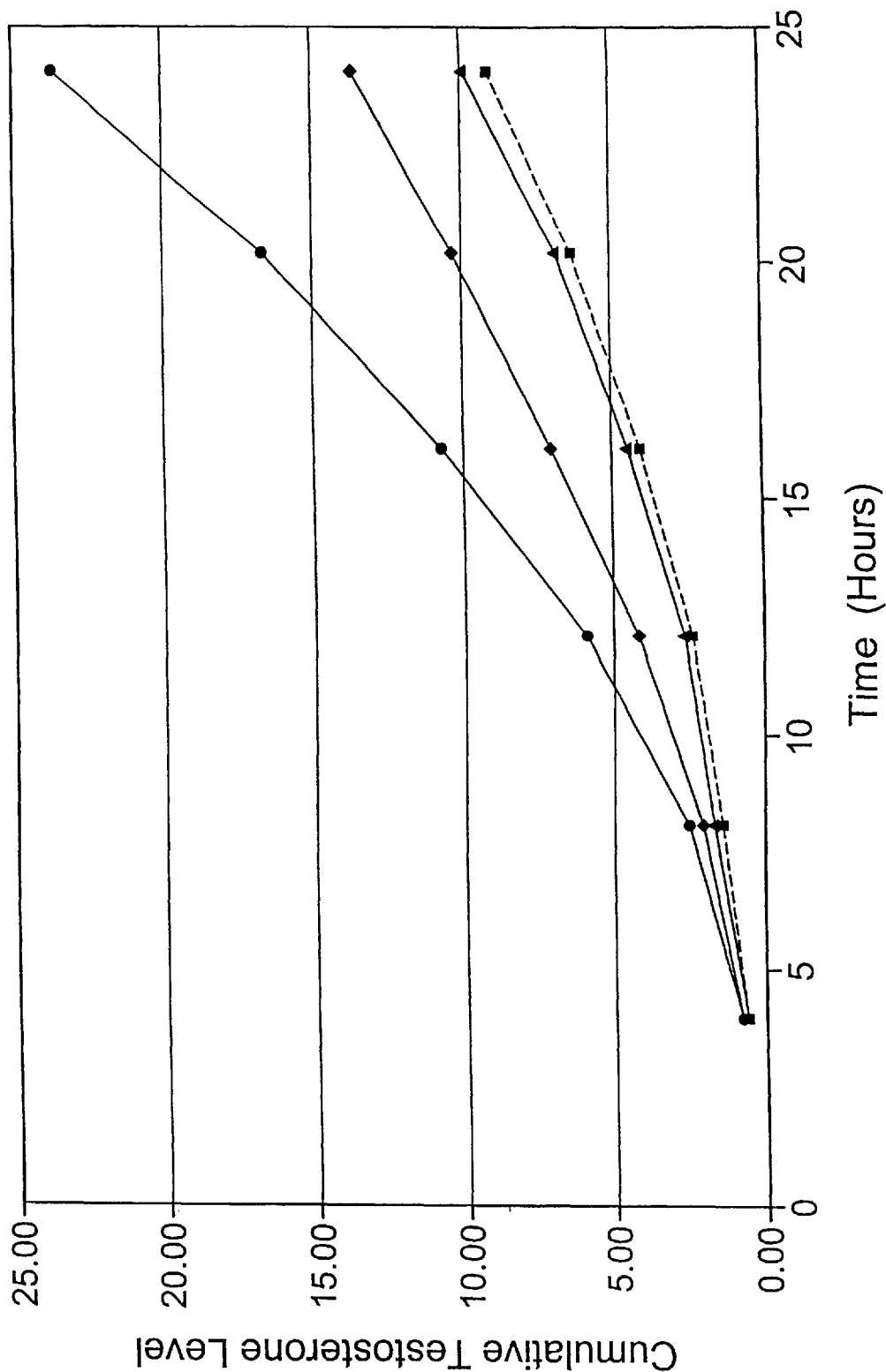
FIG. 1 illustrates the cumulative testosterone levels in a receiver reservoir delivered from three topical formulations compared to a commercial patch gel across excised pig skin.

In certain aspects, the present invention relates to transdermal and topical drug delivery. In particular, using this mode of drug delivery, enhancement of the penetration of topically applied drugs is typically accompanied by an increase in skin irritation. As such, in one aspect, the present invention relates to a composition for topical application having penetration-enhancing properties, the composition comprising: a) an active agent; b) a penetration-enhancing system comprising: (i) a membrane fluidizer; (ii) a $C_1$–$C_4$ alcohol; and (iii) a glycol. In certain embodiments, the composition further comprises (iv) a gelling agent. This penetration enhancing system of the present invention increases transdermal and topical drug delivery while decreasing skin irritation, thereby allowing high levels of drug delivery to be achieved without causing unacceptable adverse skin reactions.

The active ingredients of the present invention can include all types of therapeutic drugs or other compounds. The active ingredients include both systemically active agents as well as topically active agents. Systemically active agents induce a biological response upon entering the blood stream. Topically active agents refer to compounds that induce a biologic response in the skin or mucous membrane.

Systemically active agents include, but are not limited to, anti-infectives such as antibiotics and antiviral agents, analgesics and analgesic combinations, anorexics and appetite suppressants, anthelmintics, anesthetics, antiarthritics, antiasthma agents, anticonvulsants, antidepressants, antidiabetic agents, antidiarrheals, antihistamines, anti-inflammatory agents, antimigraine preparations, antimotion sickness agents, antinauseants, antineoplastics, antiparkinsonism agents, antipruritics, antipsychotics, antipyretics, antispasmodics, anticholinergics, sympathomimetics, xanthine derivatives, cardiovascular preparations including calcium channel blockers, beta blockers, antiarrhythmics, antihypertensives, diuretics, vasodilators (general, coronary, peripheral and cerebral), central nervous system stimulants, cough and cold preparations, decongestants, diagnostics, hormones, hypnotics, immunosuppressives, muscle relaxants, parasympatholytics, parasympathomimetics, psychostimulants, sedatives, tranquilizers, antioxidants, vitamins, minerals, other nutrients, and herbal extracts or preparations.

Topically active agents include, but are not limited to, anti-inflammatory agents, anti-infectives, analgesics, anesthetics, antihistamines, photoprotective agents, antineoplastics, antipruritics, neuropeptides, channel blockers, hydrocarbon compositions, hormones, vitamins, minerals, antioxidants, other nutrients, herbal extracts or preparations, and cosmetic ingredients. Certain agents listed above are active both systemically and in the skin and mucous membrane.

The amount of systemically and/or topically active agent included in the formulation is subject to the degree to which penetration enhancement is achieved. When the increase in penetration is relatively large, lesser amounts of the active agent can be used. With these considerations, the appropriate amounts or concentrations in any given instance will be readily apparent to the skilled physician prescribing the formulation or to the formulator preparing the formulation for use by the lay person.

In a preferred embodiment, the active agent is a mammalian sex hormone, hormone derivative, or hormone mimetic. Examples include, but are not limited testosterone or estradiol. The active ingredient is present in the composition in about 0.1% to about 10% weight to weight. Preferably, from about 0.1% to about 5%, and more preferably, from about 1% to about 2% weight to weight of the composition.

The compositions of the present invention include oleic acid. Oleic acid (cis-9-octadecenoic acid) is a monounsaturated fatty acid. Oleic acid is present from about 0.1% to about 10% weight to weight of the composition, preferably it is present from about 0.1% to about 5% weight to weight of the composition. The ability of oleic acid to lessen the irritation caused by other penetration enhancing agents and/or other formulation components to a greater extent than oleyl alcohol has not been described previously. By adding oleic acid to the compositions of the present invention, such as testosterone formulations, the skin irritation caused by these formulations is markedly reduced. Surprisingly, the combination of oleic acid with a gelling agent, such as CARBOPOL® (a polyacrylic acid), and/or other irritation reducing agents results in formulations that produce unexpectedly low levels of skin irritation.

Before the advent of the present invention, it was believed that oleic acid, oleyl alcohol and esters of oleic acid were all equal in their ability to enhance penetration and reduce skin irritation. Surprisingly, it has now been discovered that oleic acid is far superior to oleyl alcohol in its ability to reduce skin irritation. This is especially true when oleic acid is used in combination with a gelling agent.

In addition to oleic acid, the penetrating enhancing system of the present invention contains an alcohol. As used herein the term "alcohol" refers to a monohydric alcohol, preferably an aliphatic alcohol and more preferably a saturated monohydric aliphatic alcohol. Examples are methanol, ethanol, propanol, isopropanol, and octanol. In the present invention, a $C_1$–$C_4$ alcohol is preferred. These include, but are not limited to, ethanol, propanol, isopropanol and mixtures thereof. Mixtures include, for example, ethanol and isopropanol.

The compositions in accordance with the present invention contain an alcohol in about 5% to about 55% weight to weight of the composition. Preferably, the alcohol is present from about 10% to about 40% weight to weight and more preferably, from about 25% to about 35% weight to weight of the composition.

In addition to oleic acid and an alcohol, the penetration-enhancing system of the present invention comprises a glycol. As used herein, the term "glycol" refers to a polyhydric alcohol, preferably a dihydric alcohol. Examples are ethylene glycol, propylene glycol, butylene glycol and glycerol. Preferably, the glycol is ethylene glycol, propylene glycol, butylene glycol and mixtures thereof.

The compositions of the present invention contain a glycol in about 25% to about 55% weight to weight of the composition. Preferably, the glycol content is from about 30% to about 40% weight to weight of the composition.

In addition, the compositions of the present invention optionally comprise a gelling agent. Formulations with a gelling agent in conjunction with oleic acid were tested. Formulations containing a gelling agent, for instance, CARBOPOL® 1342 (a polyacrylic acid), produced lower levels of skin irritation than did formulations containing no gelling agent. These tests indicate that including a gelling agent in the PES maintains the system's ability to enhance topical and transdermal drug delivery, while reducing irritation associated with topical or transdermal application. This finding is quite remarkable because the inclusion of lower alcohols is known to induce skin sensitization and was heretofore believed to be unsuitable as solvents for compounds applied to the skin. Surprisingly, including a gelling agent with oleic acid resulted in lower irritation levels than formulations with oleyl alcohol and a gelling agent.

Suitable gelling agents of the present invention include, but are not limited to, Carbopol 1342, Carbopol 940, Klucel and Klucel HF. Synonyms for carbopol are carbomer, poly (1-carboxyethylene) or poly(acrylic acid). Those of skill in the art will know of other gelling agents that are suitable to practice the present invention. The gelling agent is present from about 1% to about 10% weight to weight of the composition. Preferably, the gelling agent is present from about 1% to about 5%, and more preferably, from about 1% to about 3% weight to weight of the composition.

The formulations in which the compositions of the present invention are incorporated in can assume any of a variety of dosage forms. Examples are creams, lotions, gels, ointments, suppositories, sprays, aerosols, buccal and sublingual tablets and various passive and active transdermal devices for absorption through the skin and mucous membranes.

The penetration enhancing compositions of this invention may constitute a small amount of the formulation or a large amount depending on which excipient composition is used, which systemically and/or topically active agent is used and the type of biological effect sought. The amount will be readily apparent to those skilled in the art, since the total amount of penetration enhancers will be approximately the same as those of the prior art. For example, when the potency of the penetration enhancement composition is greatly increased, lower quantities can be used.

In addition to the foregoing composition components, the compositions of the present invention can optionally contain other ingredients. For example, triethanolamine, can be added as a crosslinking agent. A preservative, such as betahydoxytoluene can be added. Other irritation reducing agents can be added. In this regard, irritation reducing agents include, but are not limited to, glycerol. In some instances, semi-solid testosterone formulations have been prepared with propylene glycol and/or butylene glycol as the glycol component, ethyl alcohol and/or isopropyl alcohol as the alcohol component. Preservatives, a cross-linking agent, and additional irritation reducing agents have been included in formulations prepared in accordance with this invention.

Various conditions and disorders are treatable, prevented, or promoted by the compositions of the present invention. Examples of conditions include, but are not limited to, treatment of conditions related to testosterone deficiency; treatment of balanitis xerotic obliterans; treatment of lichen sclerosis et atrophicus; treatment of menopausal and post-menopausal symptoms and signs; prevention and/or reduction of aging related changes to skin and mucous membranes; prevention and/or reduction of skin pigmentation; prevention and/or reduction of skin roughness, wrinkles, furrows, fragility and/or atrophy; prevention and/or reduction of nail thinning and/or fracturing; prevention and/or reduction of hair thinning and/or fracturing; prevention and/or reduction of neoplasia of the skin, mucous membranes, other epithelia, and glands; prevention and/or reduction of age-related bone demineralization; promotion of hair and/or nail growth; promotion of increased muscle size and stamina; peversal of muscle wasting; promotion of increased speed of reaction time and reversal of decreased reaction time; promotion of increased growth of appendages and organism as a whole; prevention and/or reversal of xerosis; promotion of healing or as treatment for hemorrhoids or anal fissures.

As such, in another aspect, the present invention relates to a method for administering a topically or systemically active agent, the method comprising: topically administering to a mammal a composition comprising: a) an active agent; and b) a penetration-enhancing system comprising: (i) oleic acid; (ii) a $C_1$–$C_4$ alcohol; and (iii) a glycol. In some embodiments, the penetration-enhancing system further comprises (iv) a gelling agent. In certain preferred embodiments, the method relates to treatment of conditions related to testosterone deficiency.

In yet another aspect, the present invention relates to a method of reducing inflammation associated with topical application of an active agent, the method comprising: topically administering to a mammal a composition comprising: a) an active agent; and b) a penetration-enhancing system comprising: (i) oleic acid; (ii) a $C_1$–$C_4$ alcohol; and (iii) a glycol. In some embodiments, the penetration-enhancing system further comprises (iv) a gelling agent.

Subjects to whom the formulations can be administered are primarily mammals, including humans, pets, and livestock and other farm animals. The invention is of greatest interest in its application to humans. The term "topical administration" or "topical application" refers to directly layering or spreading upon epidermal tissue, especially outer skin or membrane, including the skin or membrane of the oral or vaginal cavities.

The site of application is dependent on many factors including, but not limited to, the amount of drug to be delivered, the extent of enhancement required, the irritation response manifested and the time of application. Thus, another important facet of this invention is the use of these compositions with drugs other than for example, testosterone, or to apply such formulations, or topical products in general, specifically to the soles of the feet, the palms of the hands or other immune-privileged sites of the body. Also, the drugs, compositions or products may be administered later in the day or at night when the permeability at the site of application is higher.

The in vitro evaluation of compositions of the present invention can be accomplished using a variety of skin diffusion cell experimental protocols. (See, for example, "Transdermal Drug Delivery" Ed. Jonathan Hadgraft et al., Chapter 9, Marcel Dekker Inc., New York; Bronaugh et al., *J Phar. Sci.*, 75:1094–1097, (1986); and Bronaugh et al., *J. Phar. Sci.*, 74: 64–67, (1985)). In general in vitro transdermal delivery experiments are conducted on either vertically or horizontally arranged diffusion cells. It is desirable to control various environmental factors that can effect the rate of diffusion. The factors include, for instance, temperature. This is because the rate of diffusion will increase with increasing temperature. Thus, it is important to consider various factors related to the skin surface including, skin surface coverings, microorganisms, vehicle formulation and duration of contact with the skin.

The transdermal delivery experiments are conducted by applying a finite amount of drug formulation onto the skin sample. The skin is placed on top of a flow-through permeation cell. Once the candidate molecule has penetrated through the stratum corneum, it will be transported it its proposed site of action. Typically, for in vitro experiments, the body mass is represented by physiological saline. The diffusion cell contains a receptor compartment, and typically the compartment is made as small as possible. After the molecule has penetrated the skin it is collected for assay. The most widely used assay procedure for studying transdermal delivery is radioactive labeling. There exist a number of methods for identifying the distribution of the penetrant within the skin during the course of penetrations. These include, for example, tape stripping, autoradiographs, and skin sectioning. Using the flow-through permeation cell experiments describe above, the in vitro evaluation of formulations of the present invention can be accomplished by a person skilled in the art.

In addition to in vitro evaluation, in vivo evaluations of the formulations of the present invention have also been conducted. In these evaluations, New Zealand white albino rabbits are used. Each animal receives 100 mg/cm$^2$ of the test material twice a day for five consecutive days. Six to eight hours following the first dose of the day, a second dose is administered on the same site to each rabbit. The test material is applied to the skin undiluted.

Each site is then scored for evidence of erythema and edema at 24, 48 and 72 hours following the final application. A mean primary irritation score (MPI) for each test animal is calculated as follows. For each observation period, the average erythema scores were calculated by dividing the sum erythema scores for all animals. The edema scores were calculated in the same manner. The sum of the average erythema and edema scores is divided by the total number of observation periods to obtain the MPI scores.

The following examples are offered for purposes of illustration. They are intended neither to define nor to limit this invention in any manner.

EXAMPLES

Example 1

The following example illustrates a comparison between formulations using oleic acid versus oleyl alcohol as a membrane fluidizer.

Testosterone formulations, in which either oleic acid or oleyl alcohol was used as the membrane fluidizer, were tested in vitro, demonstrating equivalent levels of drug delivery. The testosterone formulations were tested and the results indicated that the formulations containing oleyl alcohol produced much higher levels of skin irritation than did the testosterone formulations containing oleic acid. These tests indicate that substituting oleic acid as the membrane fluidizer in the PES not only maintains the system's ability to enhance topical and transdermal drug delivery, but produces the unanticipated result of reduced skin irritation.

Table I lists the formulations tested, identifying each one by its ingredients followed by the weight percent of each. Average testosterone flux and total erythema score followed by standard deviations are given for each formulation. The abbreviations used in the table are as follows:

| | |
|---|---|
| T | testosterone |
| PG | propylene glycol |

-continued

| | |
|---|---|
| ET | ethyl alcohol |
| IPA | isopropyl alcohol |
| KH | Klucel HF (hydroxypropylcellulose: gelling agent) |
| O Acd | oleic acid |
| O Alc | oleyl alcohol |
| C1 | Carbopol 1342 |
| TEA | Triethanolamine |
| SD | Standard deviation |

TABLE 1

| Formulation | Formulation Components | Average Testosterone flux, ± SD | Total Erythema Score After 120 h, ± SD |
|---|---|---|---|
| A | T2, PG37, ET15, IPA15, KH1, O Acd 1.0 | 21.21 ± 1.87 | 4.0 ± 0.3 |
| B | T2, PG37, ET15, IPA15, KH1, O Alc 1.0 | 15.08 ± 3.96 | 8.7 ± 0.3 |

Table 2 illustrates a comparison between formulations using oleic acid versus oleyl alcohol. Similar to the comparison in Table I, formulations containing oleyl alcohol produced much higher levels of skin irritation than did the testosterone formulations containing oleic acid. These tests indicate that substituting oleic acid in the PES not only maintains the system's ability to enhance topical and transdermal drug delivery but produces the unanticipated result of reduced skin irritation.

TABLE 2

| Formula | Active | Glycol | Alcohol #1 | Alcohol #2 | Mbr Fluid | Gelling | Crosslnk | Water |
|---|---|---|---|---|---|---|---|---|
| 545 | T 2.0 | PG 36.6 | ET 15.0 | IPA 15.0 | OAcd 1.0 | Cl 0.6 | TEA 0.4 | 29.4 |
| 546 | T 2.0 | PG 36.6 | ET 15.0 | IPA 15.0 | OAlc 1.0 | Cl 0.6 | TEA 0.4 | 29.4 |

In this experiment, the 545 formula had a cumulative flux of 22.63 and an irritation score of 5.0, whereas the 546 formula had a cumulative flux of 18.86 and an irritation score of 9.3.

Example 2

The following example illustrates preferred compositions for gel products of the present invention.

| Ingredient | Range |
|---|---|
| Ethanol | 0.1 to 50% |
| Propylene Glycol | 0.1 to 50% |
| Isopropyl Alcohol | 0.1 to 50% |
| Oleic Acid | 0.1 to 50% |
| Gelling Agent | 0.01 to 50% |
| Additional Irritation Reducers | 0.1 to 50% |

-continued

| Ingredient | Range |
| --- | --- |
| Preservatives | 0 (the formulation may be self-preserving) to 0.1% |
| Drug | 0% to saturation |

Example 3

The following example illustrates the preferred compositions for ointment products of the present invention:

| Ingredient | Range |
| --- | --- |
| Propylene Glycol | 0.1 to 50% |
| Butylene Glycol | 0.1 to 50% |
| Isopropyl Myristate | 0.1 to 50% |
| Oleic Acid | 0.1 to 50% |
| Mygliol | 0.1 to 50% |
| Petrolatum | 0.1 to 80% |
| Polawax | 0.1 to 20% |
| Gelling Agent | 0.01 to 50% |
| Additional Irritation Reducers | 0.1 to 50% |
| Preservatives | 0 (formulation may be self-preserving) to 0.1% |
| Drug | 0% to saturation |

Example 4

The following example illustrates preferred compositions for emulsion products of the present invention.

| Ingredient | Range |
| --- | --- |
| Deionized Water | 10 to 50% |
| Propylene Glycol | 0.1 to 50% |
| Butylene Glycol | 0.1 to 50% |
| Isopropyl Myristate | 0.1 to 30% |
| Oleic Acid | 0.1 to 20% |
| Cetyl Alcohol | 0.1 to 5% |
| Mygliol | 0.1 to 30% |
| Petrolatum | 0.1 to 80% |
| Gelling | 0.1 to 30% |
| Polawax | 0.1 to 10% |
| Additional Irritation Reducers | 0.1 to 50% |
| Preservatives | 0 (formulation may be self-preserving) to 0.1% |
| Drug | 0% to saturation |

Example 5

This example illustrates formulations in terms of ingredients and the weight percent of each ingredient.

TABLE 3

| No. | ET | IPA | PG | O Acd | T | IR | IR | Carb | TEA | Water |
| --- | --- | --- | --- | --- | --- | --- | --- | --- | --- | --- |
| J | 15.0 | 15.0 | 35.6 | 1.0 | 2.0 | 1.0 | — | 0.6 | 0.4 | 29.4 |
| K | 15.0 | 15.0 | 35.1 | 2.5 | 2.0 | — | — | 0.6 | 0.4 | 29.4 |
| L | 15.0 | 15.0 | 34.6 | 1.0 | 2.0 | 1.0 | 1.0 | 0.6 | 0.4 | 29.4 |

Example 6

This example illustrates formulations in terms of ingredients and the weight percent of each ingredient.

TABLE 4

| Formulation No. | DAA-97-602 | DAA-97-601 | DAA-97-600 |
| --- | --- | --- | --- |
| Ethanol | 15.0 | 15.0 | 15.0 |
| Isopropyl Alcohol | 15.0 | 15.0 | 15.0 |
| Propylene glycol | 35.6 | 35.1 | 34.6 |
| Oleic Acid | 1.0 | 2.5 | 2.0 |
| Testosterone | 2.0 | 2.0 | 2.0 |
| Irritation Reducing Agent No. 1 | 1.0 | — | 1.0 |
| Irritation Reducing Agent No. 2 | — | — | 1.0 |
| CARBOPOL 1342 | 0.6 | 0.6 | 0.6 |
| Triethanolamine | 0.4 | 0.4 | 0.4 |
| Water | 29.4 | 29.4 | 29.4 |

With reference to FIG. 1, the cumulative testosterone levels in a receiver reservoir delivered from the three topical formulations are compared to a commercial patch gel across excised pig skin. Formulation No. DAA-97-602 is represented by triangles, Formulation No. DAA-97-601 by diamonds, and Formulation No. DAA-97-600 is represented by squares. The circles represent the commercial patch gel.

Similar delivery profiles of these three formulations were seen using surgically removed human skin in the same skin delivery studies. Therefore, these formulations will have utility in people and other mammals suffering with systemic testosterone deficient disorders. Furthermore, these formulations can be used to deliver testosterone locally, and thus can be used in conditions where increase in local testosterone concentration is beneficial. An example of this kind of disorder is vulval lichen scelerosus.

The testosterone formulations described in this invention exhibited significantly lower levels of irritation than other marketed testosterone products, making them more acceptable to patients and thus improving compliance. These irritation studies measured both erythema (skin redness) and edema (skin swelling) development that are two hallmark features of skin inflammation. Both reactions could be primary clinical manifestations of skin inflammation, and may also be a prelude to even more severe conditions such as blister formation, necrosis, etc. While the combination of oleic acid and Carbopol 1342 produced very low irritating formulations, the incorporation of other irritation reducing agents can further decrease irritation. These anti-irritation approaches can thus be used in combination in testosterone-delivering formulations, or any other topical product or dosage form. Thus, they have utility in minimizing irritation for all pharmaceutical; cosmeceutical or general skin care formulations.

Example 8

Using a computer model, this example optimizes the '601 formulation by adjusting (1) testosterone concentration and (2) pH.

Statistical design: In this example, the pH range was set from 3 to 6, and testosterone concentration range was set from 0.5% to 2.0%. With these two definitions, the statistical software Echip ran through 16 unique formulations in order to identify the optimal pH and concentration for testosterone delivery.

FORMULATION COMPOSITIONS:

| Ingredient | 0.50%<br>Form.<br>#1:6.0<br>Form.<br>#2:4.5<br>Form.<br>#6:3.0 | 1.00%<br>Form.<br>#11:5.0<br>Form.<br>#8:3.0<br>Form.<br>#14:6.0<br>Form.<br>15:7.0<br>Form.<br>16:8.0 | 1.25%<br>Form.<br>#3:6.0 | 1.50%<br>Form.<br>#7:3.0 | 2.00%<br>Form. #4:6.0<br>Form. #5:3.0<br>Form. #9:4.0<br>Form. #10:5.0<br>Form. #12:7.0<br>Form. #13:8.0 |
|---|---|---|---|---|---|
| Testosterone USP/NF | 0.50 | 1.00 | 1.25 | 1.50 | 2.00 |
| Carbomer 1342 USP | 0.60 | 0.60 | 0.60 | 0.60 | 0.60 |
| Propylene Glycol USP | 35.61 | 35.44 | 35.33 | 35.23 | 35.05 |
| Isopropyl Alcohol USP | 15.24 | 15.16 | 15.12 | 15.08 | 15.00 | single donor was used and n=5–6 replicates were used for each formulation.

In this experiment, fresh human skin was obtained from local cosmetic surgeons, dermatomed within 24 hours at a thickness of 500 μm, and stored frozen at −80° C. (1 week to 8 months). Before each experiment, the skin was thawed at 4° C. for about 16 hours, at room temperature for about 1 hour and mounted in 1-cm² flow-through diffusion cells. Flow rate was set to 3 ml/hr, and receptor phase was saline at 32° C. All cells were non-occluded and 10 mg of formulation was applied at time 0 (dose=10 mg/cm²). In each study, all formulations were spiked with $^{14}$C-testosterone (~2000 or 20,000 DPM per 10 mg dose). Both flux (6 time points, every 4 hours for 24 hours, analysis: HPLC) and skin content data were obtained (an alcoholic swab of the surface, 2 tape-strips, and the rest of the skin sample digested in NaOH, analysis: scintillation counting).

RESULTS:

The results indicated that formulations having a pH from about 5 to about 6 gave the optimum formulations.

| Formulations | | Study # | Amount testosterone permeated in 24 hours (ug/cm²) | | Residue on skin - alcoholic swab - (ug/cm²) | | Residue on skin - tape strips - (ug/cm²) | | Amount in skin (ug/g tissue) | |
|---|---|---|---|---|---|---|---|---|---|---|
| code | composition and pH | | average | s.d. | average | s.d. | average | s.d. | average | s.d. |
| #4 (601) | 2.00% test., pH 6.0 | 1 | 24.31 | 3.98 | 55.4 | 15.9 | 18.7 | 11.2 | 409.3 | 112.5 |
| | | 2 | 31.36 | 6.09 | 59.8 | 22.3 | 19.6 | 6.6 | 257.3 | 71.4 |
| | | 3 | 22.76 | 4.02 | 57.2 | 20.2 | 15.0 | 7.2 | 267.1 | 63.7 |
| | | 4 | 46.96 | 14.19 | 79.3 | 5.8 | 21.4 | 7.0 | 726.8 | 111.5 |
| | | 5 | 35.45 | 5.63 | 51.2* | 13.4* | 29.9 | 6.3 | 439.0 | 159.4 |

*alcoholic swab taken after a dry swab

-continued

FORMULATION COMPOSITIONS:

| Ingredient | 0.50%<br>Form.<br>#1:6.0<br>Form.<br>#2:4.5<br>Form.<br>#6:3.0 | 1.00%<br>Form.<br>#11:5.0<br>Form.<br>#8:3.0<br>Form.<br>#14:6.0<br>Form.<br>15:7.0<br>Form.<br>16:8.0 | 1.25%<br>Form.<br>#3:6.0 | 1.50%<br>Form.<br>#7:3.0 | 2.00%<br>Form. #4:6.0<br>Form. #5:3.0<br>Form. #9:4.0<br>Form. #10:5.0<br>Form. #12:7.0<br>Form. #13:8.0 |
|---|---|---|---|---|---|
| Dehydrated alcohol USP | 15.24 | 15.16 | 15.12 | 15.08 | 15.00 |
| Oleic acid USP | 2.50 | 2.50 | 2.50 | 2.50 | 2.50 |
| Triethanolamine 99% NF or HCl 1N | qs to pH | qs to pH | qs to pH | qs to pH | qs to pH |
| Butylated Hydroxytoluene, NF | 0.050 | 0.050 | 0.050 | 0.050 | 0.050 |
| Purified water, USP | 29.87 | 29.72 | 29.64 | 29.54 | 29.40 |

Since the 16 formulations (22 runs) could not be all tested on skin from a single donor; instead four separate studies were conducted. Study #5 was added to further investigate differences between pH 5 and 6. In each study, skin from a None of the formulations delivered an amount of testosterone significantly higher than that delivered by 601 (2% testosterone, pH 6.0). However, there seemed to be a trend for formulations at pH 5.0 to be consistently better—although not significantly—than the corresponding formulation at pH 6.0.

The same conclusion is further illustrated quantitatively in the table below: Enhancement ratios for all studies (1–5) were calculated with reference to 601 (i.e. cumulative amount permeated at 24 hours for formulation X divided by cumulative amount permeated at 24 hours from 601). These ratios were calculated at different pHs for 2 concentrations of testosterone (without concentration correction) from data obtained with same skin donor (i.e. in the same study).

In the table below, flux and skin analysis data were used to project the required area for the delivery of 5 mg/day and the amount of residue left on and in the skin if 1 g/100 cm² of gel was applied to such area.

| | In vitro cumulative amount permeated in 24 hours (ug/cm², mean ± SD, n = 5–6) | Required area for the delivery of 5 mg per day | Total testosterone dosed (1 g of gel per 100 cm²) | Residue left on skin after 24 hours (swab + tape strips) | Testosterone left in dosed skin after 24 hours |
|---|---|---|---|---|---|
| 2.0% gel pH 6.0 (form. 4) | 47.0 ± 14.2 | 106 cm² | 21.2 mg (100%) | 10.7 mg (49 ± 5%) | 2.8 mg (13 ± 4%) |
| 1.0% gel pH 6.0 (form. 14) | 28.0 ± 4.8 | 178 cm² | 17.8 mg (100%) | 5.7 mg (32 ± 4%) | 2.5 mg (14 ± 2%) |

Example 9

Clinical Formulations of Testosterone Topical Gel

| | % w/w | |
|---|---|---|
| INGREDIENTS | 1.0% | 2.0% |
| Testosterone, USP/NF | 1.00 | 2.00 |
| Ethanol, Dehydrated USP | 15.00 | 15.00 |
| 2-Propanol, USP | 15.00 | 15.00 |
| Propylene Glycol, USP | 35.05 | 35.05 |
| Oleic Acid, NF | 2.50 | 2.50 |
| Butylated Hydroxytoluene, NF | 0.05 | 0.05 |
| Carbomer, USP | 0.60 | 0.60 |
| Triethanolamine, NF q.s. to pH 6.0 | 0.30–0.40 | 0.30–0.40 |
| Purified Water, USP q.s. | 30.00–29.90 | 29.00–28.90 |
| Total | 100.00 | 100.0 |

| | Gram/20-Kg Batch | |
|---|---|---|
| INGREDIENTS | 1.0% | 2.0% |
| Testosterone, USP/NF | 200.00 | 400.00 |
| Ethanol, Dehydrated[3] USP/NF | 3000.00 | 3000.00 |
| 2-Propanol, USP | 3000.00 | 3000.00 |
| Propylene Glycol, USP | 7010.00 | 7010.00 |
| Oleic Acid, NF | 500.00 | 500.00 |
| Butylated Hydroxytoluene, NF | 10.00 | 10.00 |
| Carbomer[4], USP | 120.00 | 120.00 |
| Triethanolamine[5], NF q.s. | 60.00–80.00 | 60.00–80.00 |
| Purified Water[6], USP q.s. | 6000.00–5980.00 | 5800.00–5780.00 |
| Total | 20,000.00 | 20,000.00 |

Typical Manufacturing Procedure for the Clinical Formulations Procedure for the preparation of a typical batch of 1.0% or 2.0% testosterone topical gel:

1) Charge 95% of purified water, USP to a suitable vessel and ad Carbomer, USP with mixing. Mix the slurry at 20–30° C. until the Carbomer is completely dispersed and hydrated.
2) Add dehydrated ethanol, USP, 2-propanol, USP, oleic acid, butylated hydroxytoluene, NF, testosterone, USP/NF and propylene glycol, USP to the primary compounding vessel. After each addition, the mixture is stirred to complete dissolution.
3) Add the entire amount of Carbomer gel to the compounding vessel with good stirring. Add triethanolamine, NF slowly with mixing to thicken the gel.
4) Check the pH and adjust the pH to target using extra triethanolamine, NF or 1.0 N HCI, USP, if necessary. Then q.s. to the final weight with purified water, USP.
5) Samples are taken from top, middle and bottom of the compounding vessel for in-process assays for testosterone, ethanol and pH.
6) Fill the bulk gel into containers/bottles.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A method for administering a topically or systemically active agent with increased penetration, said method comprising: topically administering to a mammal a composition comprising:
    a) an active agent having a concentration of about 0.1% to about 2%, wherein said active agent is a member selected from the group consisting of testosterone, estradiol, derivatives thereof and the mixture thereof;
    b) a penetration-enhancing system consisting essentially of (i) a membrane fluidizer comprising oleic acid; (ii) a $C_1$–$C_4$ alcohol; and (iii) a glycol said composition having a pH value of between about 4 to about 8, thereby administering a topically or systemically active agent with increased penetration.

2. A method in accordance with claim 1, wherein said penetration-enhancing system further comprises (iv) a gelling agent.

3. A method in accordance with claim 1, wherein said active agent is testosterone.

4. A method in accordance with claim 1, wherein said active agent is testosterone propionate.

5. A method for reducing inflammation associated with topical application of a topically or systemically active agent, said method comprising: topically administering to a mammal a composition comprising: a) an active agent having a concentration of about 0.1% to about 2%, wherein said active agent is a member selected from the group consisting of testosterone, estradiol, derivatives thereof and the mixture thereof; b) a penetration-enhancing system consisting essentially of (i) a membrane fluidizer comprising oleic acid; (ii) a $C_1$–$C_4$ alcohol; and (iii) a glycol said composition having a pH value of between about 4 to about 8, thereby reducing inflammation associated with a topical application of a topically or systemically active agent.

6. A method in accordance with claim 5, wherein said penetration-enhancing system further comprises (iv) a gelling agent.

7. A method in accordance with claim 6, wherein said active agent is a member selected from the group consisting of testosterone, testosterone propionate and mixtures thereof.

8. A method in accordance with claim 7, wherein said active agent is testosterone propionate.

9. A method in accordance with claim 1, wherein said pH value is between about 4.5 to about 6.5.

10. A method in accordance with claim 1, wherein said active agent is present in a concentration selected from the group consisting of 0.5%, 1.00%, 1.25%, 1.50% and 2.00% weight to weight of said composition.

11. A method in accordance with claim 1, wherein said $C_1$-$C_4$ alcohol is isopropanol.

12. A method in accordance with claim 1, wherein said glycol is propylene glycol.

13. A method in accordance with claim 1, wherein said gelling agent is Carbopol 1342.

14. A method in accordance with claim 1, wherein said penetration enhancing system fmal urther comprises an irritation reducing agent.

15. A method in accordance with claim 1, wherein said active agent is a mixture of testosterone and estradiol.

16. A method in accordance with claim 5, wherein said active agent is testosterone.

17. A method in accordance with claim 5, wherein said active agent is a mixture of testosterone and estradiol.

18. A method in accordance with claim 5, wherein said penetration enhancing system further comprises an iritation reducing agent.

19. A method for administering a topically or systemically active agent with increased penetration, said method comprising: topically administering to a mammal a composition comprising:
   a) testosterone or a derivative thereof having a concentration of about 0.1% to about 2%;
   b) a penetration-enhancing system comprising: (i) oleic acid; (ii) a $C_3$ alcohol; and (iii) propylene glycol thereby administering a topically or systemically active agent with increased penetration.

20. A method in accordance with claim 19, wherein testosterone or a derivative thereof is present in a concentration selected from the group consisting of 0.5%, 1.00%, 1.25%, 1.50% and 2.00% weight to weight of said composition.

21. A method in accordance with claim 19, wherein said penetration-enhancing system further comprises (iv) a gelling agent.

22. A method for administering a topically or systemically active agent with increased penetration, said method comprising: topically administering to a mammal a composition comprising:
   a) estradiol or a derivative thereof having a concentration of about 0.1% to about 10%;
   b) a penetration-enhancing system comprising: (i) oleic acid; (ii) a $C_3$ alcohol; and (iii) propylene glycol, thereby administering a topically or systemically active agent with increased penetration.

23. A method in accordance with claim 22, wherein estradiol or a derivative thereof is present from about 0.1% to about 5% weight to weight of said composition.

24. A method in accordance with claim 22, wherein estradiol or a derivative thereof is present from about 1% to about 2% weight to weight of said composition.

25. A method in accordance with claim 22, wherein estradiol or a derivative thereof is present in a concentration selected from the group consisting of 0.5%, 1.00%, 1.25%, 1.50% and 2.00% weight to weight of said composition.

26. A method in accordance with claim 22, wherein said penetration-enhancing system further comprises (iv) a gelling agent.

* * * * *